United States Patent [19]

Foldesy

[11] Patent Number: 4,988,736
[45] Date of Patent: Jan. 29, 1991

[54] USE OF D-PROPRANOLOL AGAINST SEXUALLY TRANSMITTED BACTERIA

[75] Inventor: Robin G. Foldesy, Raleigh, N.C.

[73] Assignee: Family Health International, Durham, N.C.

[21] Appl. No.: 424,399

[22] Filed: Oct. 20, 1989

[51] Int. Cl.$^5$ .......................................... A61K 31/135
[52] U.S. Cl. ..................................... 514/652; 514/932
[58] Field of Search ............................... 514/652, 932

[56] References Cited

U.S. PATENT DOCUMENTS

| 4,394,390 | 7/1983 | Hussain et al. | 514/652 |
| 4,600,708 | 7/1986 | Reuter et al. | 514/652 |
| 4,681,899 | 7/1987 | Ohnishi | 514/652 |
| 4,795,761 | 1/1989 | Curtis-Prior et al. | 514/652 |

FOREIGN PATENT DOCUMENTS

| 1136918 | 12/1968 | United Kingdom | 514/652 |

*Primary Examiner*—Allen J. Robinson
*Attorney, Agent, or Firm*—Olive & Olive

[57] ABSTRACT

A method of inhibiting sexually transmitted bacteria, such as in gonococcal infections is disclosed, comprising contacting the bacteria with a composition containing D-propranolol, or a pharmaceutically acceptable salt thereof, preferably in a concentration of about 1% to abot 10% and lacking a polyethoxyethanol component.

14 Claims, No Drawings

USE OF D-PROPRANOLOL AGAINST SEXUALLY TRANSMITTED BACTERIA

BACKGROUND OF THE INVENTION

1. Field of the Invention

This invention relates to antimicrobial substances, and in particular, relates to compositions effective in inhibiting sexually transmitted bacteria, such as gonococci.

2. Description of the Related Art

Genital tract infections caused by pathogens such as the gonococci (*Neisseria gonorrhoeae*) and other sexually transmitted diseases (STDs) are difficult to cure once the infection has occurred, and it is difficult to prevent the spread of such infections particularly by sexual transmission. A wide variety of products have been developed to treat infections due to sexually transmitted bacteria, such as gonococci, including ampicillin, procaine penicillin G and ceftriaxone.

Many of the therapeutic agents once used to treat sexually transmitted bacterial infections have become decreasingly effective as the bacteria have developed increased chromosomally-mediated and plasmid-mediated resistance. For example, certain penicillin-resistant strains of *N. gonorrhoeae* have achieved epidemic proportions in certain parts of the United States.

Some compounds with general antibacterial activity, such as benzalkonium chloride and chlorhexidine digluconate, are also known to have spermicidal activity. Nonoxynol-9, a spermicidal contraceptive, is known to have some antiviral and antibacterial activity. Generally, however, the compositions and devices, that have been developed as contraceptives, including oral contraceptives, spermicides, and barrier methods and devices such as condoms, diaphragms and contraceptive sponges, do not possess potent activity in inhibiting microorganisms that cause STDs. Although the proper use of some contraceptive devices such as condoms provides a barrier to the further spread of STDs, condoms do not provide a means for inhibiting bacterial activity once an infection has occurred.

Nonoxynol-9, and other polyethoxyethanol compounds have been widely used as spermicides. Recently, D-propranolol and related compounds with beta-adrenergic blocking activity have been incorporated into the nonoxynol compositions, to decrease the tissue irritation caused by the nonoxynol itself. U.S. Pat. No. 4,795,761. When propranolol was incorporated into the nonoxynol-9 composition to decrease the tissue irritation, a surprising synergistic effect on spermicidal activity was noted; however, the D-propranolol by itself was found to have reduced spermicidal activity as compared to the nonoxynol-9 by itself, or to the combination of the two components. Propranolol was not known to have antibacterial activity nor to inhibit STD microorganisms such as *N. gonorrhoeae* prior to this study. The above-cited patent and all other patents and publications cited herein are hereby incorporated by reference.

DL-propranolol has also been found to inhibit motility of spermatozoa (Peterson and Freund, Biol. of Repro. 13: 552–556, 1975) and undissolved propranolol tablets (Inderal TM) were found to have potential as a vaginally applied contraceptive (Zipper et al., Brit. Med. J. 287: 1245–1246, 1983).

Because of the inhibitory effect of propranolol on sperm motility, the inhibitory activity of propranolol on protozoan flagellar activity and growth has been investigated. D-propranolol at about $10^{-3}$ moles/liter in a tissue culture medium inhibited motility and growth of *Giardia lamblia* and *Trichomonas vaginalis* (Farthing et al., J. Antimicrobial Chemotherapy 20: 519–522, 1987).

Although propranolol has spermicidal characteristics, it is much less potent as a spermicide than nonoxynol-9. Data published by Chijioke et al. (Contraception 34: 207–211, 1986) demonstrate that nonoxynol-9 is about four times more potent in vitro as a spermicide than D-propranolol. Similar in vitro results obtained by P. M. Saling (unpublished, Final Report entitled "Spermicidal Effect of D-propranolol," January, 987), showed that semen samples treated with several concentrations of nonoxynol-9 always had a lower percentage of motile sperm than those treated with the respective concentrations of D-propranolol.

It is therefore an object of this invention to provide a method of treatment with a composition that is inhibitory to sexually transmitted bacteria.

It is a further object of this invention to provide a method for inhibiting sexually transmitted bacteria that also is capable of providing contraceptive protection.

Other objects and advantages will be more fully apparent from the following discharge and appended claims.

SUMMARY OF THE INVENTION

In a broad aspect, the invention relates to a method of inhibiting bacterial activity, such as in gonococcal infections, comprising contacting the bacteria with a bacterially-inhibitory amount of D-propranolol or a pharmaceutically acceptable salt thereof.

In a preferred aspect, the bacteria are contacted by means of treatment of the infected area with a solution of about 1% to about 10% D-propranolol in an appropriate solvent, such as by topical perigenital or intravaginal application of the composition of the invention, or by application of the composition to condoms or other contraceptive devices.

The preferred composition used in the method of the invention does not contain a polyethoxyethanol, such as a nonoxynol because of the low bactericidal activity of nonoxynol-9, and because such inclusion might lead to low level irritation of localized tissue in those persons sensitive to polyethoxyethanol compounds.

Other aspects and features of the invention will be more fully apparent from the following disclosure and appended claims.

DETAILED DESCRIPTION OF THE INVENTION AND PREFERRED EMBODIMENTS THEREOF

The present invention is based on the surprising and unexpected discovery that D-propranolol, or a pharmaceutically acceptable salt thereof, may be employed as a prophylactic measure to inhibit sexually transmitted bacteria. In a preferred embodiment, the composition comprises D-propranolol, or a pharmaceutically acceptable salt thereof, in the absence of a polyethoxyethanol.

D-propranolol, or 1-(isopropylamino)-3-(1-naphthyloxy)-2-propanol as it is referred to in IUPAC nomenclature, is a water soluble compound whose corresponding L-isomer is a member of a class of beta-adrenergic receptor blocking drugs, more commonly referred to as "beta-blockers" because they inhibit the response of nervous-system receptors to adrenalin and other stimulating hormones, and which are used as a treatment for various cardiac disorders, such as hypertension, angina pectoris, and cardiac arrhythmias.

D, L-propranolol hydrochloride is widely marketed in the United States under the trademark "Inderal ™" as a treatment for such cardiac disorders; this commercially available medication is a racemic mixture of the D- and L-stereoisomers of propranolol hydrochloride. Recently, a composition containing D-propranolol in conjunction with nonoxynol-9 has been found effective as a spermicide.

The high levels of bactericidal activity of D-propranolol reported herein are very unexpected, particularly in view of the low levels of bactericidal activity that were observed for nonoxynol-9. The lack of previous reports of antibacterial activity, especially antigonococcal activity, as associated with D-propranolol or the salts thereof, together with the previous reports of relatively low spermicidal activity of D-propranolol as compared to that of the known contraceptive nonoxynol-9, would lead one to predict that D-propranolol would be very unlikely to exhibit potent bactericidal activity, and would be most unlikely to have significantly higher bactericidal activity than nonoxynol-9.

When referred to generally hereafter, it will be understood that the term "D-propranolol" refers to D-propranolol per se i.e., 1-(isopropylamino)-3-(1-naphthyloxy)-2-propanol, as well as any and all pharmaceutically acceptable salts thereof useful in the practice of the present invention. A preferred salt form of D-propranolol is as D-propranolol hydrochloride, i.e., 1-(isopropylamino)- 3-1-naphthyloxy)-2-propanol hydrochloride. Primarily because of its increased solubility in carriers, D-propranolol hydrochloride is preferred over D-propranolol per se in the method of the invention.

Substantially pure D-propranolol may be produced for subsequent use in the invention, by isolating the D-isomer from a D,L- racemic mixture of propranolol via the process disclosed in U.S. Pat. No. 3,857,889 to Thomas Leigh, issued December 31, 1974, and assigned to Imperial Chemical Industries, Ltd.

Compositions having anti-bacterial activity used according to the invention, comprising D-propranolol, may be formulated to include any of a variety of pharmaceutically acceptable carriers, and can thus be formulated as foams, jellies, creams, suppositories, aerosols, soluble film-forming materials, and the like, which may be utilized by themselves, for example, intravaginally.

The inhibitory compositions may be utilized in conjunction with barrier contraceptive devices such as diaphragms, sponges, cervical cap devices, and condoms. Such barrier devices, having surfaces which come into contact with the seminal fluids and/or other surfaces which come into contact with the vagina and with vaginal fluids may be treated with the composition according to the invention prior to use of the device by a wearer to inhibit the activity of sexually transmitted bacteria present in the fluids.

By appropriate selection of the pharmaceutical carrier employed, the compositions of the present invention may be employed in a wide variety of specific forms and modes for contacting sexually transmitted bacteria. Pharmaceutically acceptable carriers may be similar to and include carriers that are used for contraceptive compositions as are described in U.S. Pat. No. 4,432,967.

A particularly preferred mode of use of the compositions of the invention is as a topical intravaginal antibacterial inhibitor, in a concentration of about 1% to about 10% by weight D-propranolol, or pharmaceutically acceptable salt thereof, in solution or suspension in a gel or cream formulation. A pharmaceutically acceptable salt, for example, D-propranolol hydrochloride, is preferred. The same preferred formulation may be applied perigenitally, that is, in the genital area of persons of either sex. Although the concentrations of propranolol required to inhibit activity of $N.$ gonorrhoeae in vitro are far less than 1%, clinical use of a pharmaceutical preparation having a concentration of 1–10% in an appropriate gel or cream would be expected to have maximum efficacy.

If a polyethoxyethanol component such as nonoxynol-9 is included in the composition used in the method of invention, the concentration of said polyethoxyethanol component is preferably less than one per cent of the concentration of the propranolol component in the composition and most preferably less than 0.1 mM (less than 0.006% of the entire composition including the carrier and propranolol component).

The antibacterial inhibitory activity of the D-propranolol, which is known to have spermicidal activity, indicates that use of this compound may provide a double benefit of spermicidal action plus usefulness against one of the principal causes of STDs, $N.$ gonorrhoeae.

The bacterially inhibitory composition used in the method of the invention may also comprise any of a variety of further additives, such as binders, stabilizers, antioxidants, solvents, perfumes, extenders, fillers, thixotropic agents, and the like.

The features and advantages of the present invention will be more clearly understood by reference to the following non-limiting examples, wherein all parts are by weight unless otherwise specifically stated and which are not to be construed as limiting the invention.

EXAMPLE I

Preparation of Media for Testing Inhibition of Gonococcal Activity

Inhibition of gonococcal activity is tested by a reference agar dilution procedure on GC agar base, as described in National Committee for Clinical Laboratory Standards (NCCLS) (1989), Standard Methods for Dilution Antimicrobial Susceptibility Tests for Bacteria Which Grow Aerobically. Approved Standard M7-A2. National Committee for Clinical Laboratory Standards, Villanova, Pa.

GC agar base, a standard gonococcal agar, obtainable from BBL Microbiology (Cockeysville, Md.), Difco Laboratories (Detroit, Mich.), and Gibco Laboratories (Grand Island, N.Y.) is prepared according to manufacturer's recommendations. The GC agar is supplemented with 1% of a GC Supplementation reagent which contains (per liter): 1.1 g L-cysteine; 0.03 g guanine HCl; 3 mg thiamine HCl; 13 mg PABA (P-aminobenzoic acid); 0.01 g vitamin $B_{12}$; 0.1 g cocarboxylase; 0.25 g AND; 1 g adenine; 10 g L-glutamine; 100g glucose and 0.02 g ferric citrate. (termed "cysteine free" relative to other supplements).

The compound to be tested for antigonococcal activity is tested by the agar dilution method in the supplemented GC agar medium according to the above-referenced NCCLS procedure, wherein inoculated test media are incubated in 3–7% $CO_2$ and the results are interpreted at 20-24 hours. Using this procedure, the Minimal Inhibitory Concentration (MIC) is determined by standard microbial MIC analysis techniques including calculation of the lowest concentration of the tested compound that inhibited gonococcal growth. All compounds tested are diluted to a test range of 40 to 10,000 ug/ml (0.004% to 1%) in the reference agar.

Table 1 shows the results of tests with seven compounds, all of which have been reported to have some level of spermicidal activity. The compounds tested were benzalkonium chloride, chlorhexidine digluconate, D-propranolol HCl, muhric acid, menfegol, nonoxynol-9, and octoxynol-9. Chlorhexidine digluconate (Hibiclens®) is used as a disinfectant in surgical scrub procedures, and both this compound and benzalkonium chloride are known to have bactericidal action, and therefore these two compounds served as positive controls in this study.

Preliminary solubility experiments indicated that menfegol, nonoxynol-9, octoxynol-9, muhric acid and D-propranolol were fully compatible with the aqueous diluents and agar dilution test system (less than 1% or 10,000 ug/ml), while white or milky precipitates were observed with benzalkonium chloride and chlorhexidine digluconate when these were added to the agar base.

EXAMPLE II

Inoculum Preparation

All gonococcal isolates were originally cultured from clinical gonococcal infections and included strains representing various antibiotic resistance mechanisms. The 20 strains comprised 4 penicillinase producing *N. gonorrhoeae* strains, 4 penicillin-susceptible *N. gonorrhoeae* strains, 4 penicillin-resistant beta-lactamase-negative *N. gonorrhoeae* strains, and 8 strains from clinical cases of gonorrhoea cultured within one year prior to the study. As noted in Table 1, some of the strains were also resistant to spectinomycin and tetracycline.

EXAMPLE III

Minimum Inhibitory Concentrations of Tested Compounds

As shown in Table 1, the compounds that were tested generally had three levels of anti-gonococcal activity. The most active group of compounds included benzalkonium chloride (all MICs were $\leq 40$ ug/ml), chlorhexidine digluconate (all MICs were $\leq 40$ ug/ml) and D-propranolol (MICs were $\leq 40$ to 150 ug/ml). Muhric acid was less potent, with a median MIC (MIC 50) of $>10,000$ ug/ml and a range of 150 to $>10,000$ ug/ml.

The three remaining compounds tested, menfegol, nonoxynol-9 and octoxynol-9, showed a clear bimodality of activity with all MICs either $\leq 2,500$ (0.25%) ug/ml or $>10,000$ ug/ml ($>1\%$). Most *N. gonorrhoeae* strains tested were resistant at the 1% solution level to menfegol, nonoxynol-9 and octoxynol-9. No evidence of a correlation exists between the resistances to antimicrobial agents (penicillin, tetracycline, spectinomycin) and the antimicrobial activity of the "spermicidal" drugs.

At least three of the tested compounds, benzalkonium chloride and chlorhexidine digluconate (the two positive controls) and D-propranolol, possess measurable activity against *N. gonorrhoeae* in a low percentage ($\leq 1\%$) solutions.

The most used spermicidal compound, nonoxynol-9, and related substances were not consistently potent against *N. gonorrhoeae* strains. Menfegol, another spermicidal agent, also had a more limited activity. Muhric acid has been tested as a spermicidal agent in the Far East but spermicidal potency information has been limited.

These results indicate that unlike nonoxynol-9, propranolol possesses two types of activity, "spermicidal" action and potent antibacterial activity, similar to that of known disinfectants.

TABLE 1

Minimal inhibitory concentrations (% solution) for seven antibacterial agents tested against 20 strains of *Neisseria gonorrhoeae* possessing varying degrees of susceptibility to penicillin and other drugs.

| N. gonorrhoeae susceptibility group/strain | MIC expressed as a % solution | | | | | | |
|---|---|---|---|---|---|---|---|
| | Benzalkonium chloride | Chlorhexidine | D-propranolol | Muhric Acid | Menfegol | Nonoxynol-9 | Octoxynol-9 |
| Beta-lactamase negative | | | | | | | |
| Penicillin-susceptible | | | | | | | |
| 86-36238[a] | $\leq 0.004$[b] | $\leq 0.004$ | 0.015 | 0.03 | $\leq 0.004$ | $\leq 0.004$ | 0.008 |
| 94-88[c] | $\leq 0.004$ | $\leq 0.004$ | 0.015 | 0.5 | $>1$ | $>1$ | $>1$ |
| 96-88[a] | $\leq 0.004$ | $\leq 0.004$ | 0.015 | 0.5 | $>1$ | $>1$ | $>1$ |
| 121-88 | $\leq 0.004$ | $\leq 0.004$ | 0.015 | 0.06 | $>1$ | $>1$ | 0.015 |
| Penicillin-resistant | | | | | | | |
| 93-88[a] | $\leq 0.004$ | $\leq 0.004$ | 0.015 | $>1$ | $>1$ | $>1$ | $>1$ |
| 95-88[a,c] | $\leq 0.004$ | $\leq 0.004$ | 0.015 | 0.015 | $>1$ | $>1$ | $>1$ |
| 99-88[a] | $\leq 0.004$ | $\leq 0.004$ | 0.015 | 0.5 | $>1$ | $>1$ | $>1$ |
| 102-88[a] | $\leq 0.004$ | $\leq 0.004$ | 0.015 | 1 | $>1$ | $>1$ | $>1$ |
| Clinical isolates | | | | | | | |
| 1 | $\leq 0.004$ | $\leq 0.004$ | 0.015 | 0.25 | $\leq 0.004$ | $\leq 0.004$ | 0.015 |
| 2 | $\leq 0.004$ | $\leq 0.004$ | 0.015 | 1 | $>1$ | $>1$ | $>1$ |
| 3 | $\leq 0.004$ | $\leq 0.004$ | 0.015 | 0.25 | 0.008 | 0.25 | 0.008 |
| 4 | $\leq 0.004$ | $\leq 0.004$ | 0.015 | 1 | $>1$ | $>1$ | $>1$ |
| 5 | $\leq 0.004$ | $\leq 0.004$ | $\leq 0.004$ | 0.015 | $\leq 0.004$ | $\leq 0.004$ | 0.008 |
| 6 | $\leq 0.004$ | $\leq 0.004$ | 0.015 | 1 | $>1$ | $>1$ | $>1$ |
| 7[a] | $\leq 0.004$ | $\leq 0.004$ | 0.015 | 0.5 | 1 | $>1$ | 0.015 |
| 8 | $\leq 0.004$ | $\leq 0.004$ | 0.015 | 0.25 | 0.008 | 0.008 | 0.015 |
| Beta-lactamase positive | | | | | | | |

TABLE 1-continued

Minimal inhibitory concentrations (% solution) for seven antibacterial agents tested against 20 strains of *Neisseria gonorrhoeae* possessing varying degrees of susceptibility to penicillin and other drugs.

| N. gonorrhoeae susceptibility group/strain | MIC expressed as a % solution | | | | | | |
|---|---|---|---|---|---|---|---|
| | Benzalkonium chloride | Chlorhexidine | D-propranolol | Muhric Acid | Menfegol | Nonoxynol-9 | Octoxynol-9 |
| Penicillin-resistant | | | | | | | |
| 76-61782 | ≦0.004 | ≦0.004 | 0.015 | 0.03 | ≦0.004 | ≦0.004 | ≦0.004 |
| 132-88[a] | ≦0.004 | ≦0.004 | 0.015 | 1 | >1 | >1 | >1 |
| 133-88[a] | ≦0.004 | ≦0.004 | 0.015 | 0.5 | >1 | >1 | >1 |
| 134-88[a] | ≦0.004 | ≦0.004 | 0.015 | 0.03 | ≦0.004 | ≦0.004 | ≦0.004 |

[a]These isolates were also tetracycline-resistant (MICs, ≦1 ug/ml).
[b]≦0.004% = 40 ug/ml or 0.5% = 5,000 ug/ml.
[c]These strains were resistant to spectinomycin (MICs, ≦128 ug/ml).

EXAMPLE IV

Preparation of a D-propranolol Composition

As an illustrative formulation, D-propranolol is suspended in a pharmaceutical carrier, according to the following composition, wherein the concentration of each component is expressed in per cent (weight/weight): citrate buffer (0.025M citric acid monohydrate, pH 3.0), 92.9; D-propranolol hydrochloride, 5.0; methyl p-hydroxy benzoate, 0.1; and Methocel ® E/4M methyl cellulose, 2.5. Heating the mixture to about 80° C. while the above components are added in sequence to the citrate buffer results in a smooth gel.

As the concentration of the D-propranolol hydrochloride is increased, the proportions of Methocel ® and citrate buffer are accordingly modified.

Numerous vehicle formulations other than that illustrated in this Example may be suitably employed in the method of the invention, depending on the physical character and the mode of use of the D-propranolol composition.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of inhibiting the activity of bacteria comprising exposing the bacteria to a composition comprising D-propranolol, or a pharmaceutically acceptable salt thereof, and a pharmaceutically acceptable carrier, said D-propranolol, or said pharmaceutically acceptable salt thereof being at a concentration in said pharmaceutically acceptable carrier to provide a composition effective in inhibiting sexually transmitted bacteria.

2. A method according to claim 1, wherein the composition comprises a pharmaceutically acceptable salt of D-propranolol.

3. A method according to claim 2, wherein the concentration of the pharmaceutically acceptable salt is from about 1% to about 10% by weight of the composition.

4. A method according to claim 3, wherein the pharmaceutically acceptable salt of D-propranolol is D-propranolol hydrochloride.

5. A method according to claim 1, wherein the composition comprises D-propranolol.

6. A method according to claim 5, wherein the concentration of the D-propranolol is from about 1% to about 10% by weight of the composition.

7. A method according to claim 1, wherein the bacteria are exposed to the composition by intravaginal application of the composition.

8. A method according to claim 1, wherein the bacteria are exposed to the composition by perigenital application of the composition.

9. A method according to claim 1, wherein the bacteria are exposed to the composition by application of the composition to condoms or other contraceptive devices.

10. A method according to claim 1, wherein the composition consists essentially of D-propranolol, or a pharmaceutically acceptable salt thereof, and a carrier.

11. A method according to claim 1, wherein the composition includes a polyethoxyethanol component, said component having a concentration in the composition of less than one percent of the concentration of D-propranolol, or the pharmaceutically acceptable salt thereof.

12. A method of inhibiting the activity of bacteria comprising exposing the bacteria to a composition comprising D-propranolol hydrochloride suspended in a pharmaceutically acceptable carrier at a concentration of from about 1 to about 10 per cent D-propranolol hydrochloride by weight of the composition.

13. A method of inhibiting the activity of bacteria comprising exposing the bacteria to a composition comprising D-propranolol, or a pharmaceutically acceptable salt thereof, and a pharmaceutically acceptable carrier, said D-propranolol, or said pharmaceutically acceptable salt thereof being at a concentration in said pharmaceutically acceptable carrier to provide a composition effective in inhibiting sexually transmitted bacteria, said composition being in the form of a foam, a jelly, a cream, a suppository, an aerosol, or a soluble film-forming material, or in conjunction with a barrier contraceptive device.

14. A method according to claim 13, wherein the composition consists essentially of D-propranolol, or a pharmaceutically acceptable salt thereof, and a carrier.

* * * * *